United States Patent [19]

Studenick

[11] 4,046,012
[45] Sept. 6, 1977

[54] FLUID SAMPLING DEVICE

[75] Inventor: David K. Studenick, Rockville, Md.

[73] Assignee: The United States of America as represented by the United States National Aeronautics and Space Administration, Washington, D.C.

[21] Appl. No.: 743,249

[22] Filed: Nov. 19, 1976

[51] Int. Cl.$^2$ .............................................. G01N 1/24
[52] U.S. Cl. ............................... 73/421.5 R; 250/288
[58] Field of Search ................... 73/421.5 R, 421.5 A; 250/288

[56] References Cited

U.S. PATENT DOCUMENTS

| | | | |
|---|---|---|---|
| 2,411,157 | 11/1946 | Fene et al. | 73/421.5 R |
| 2,939,126 | 5/1960 | Barghausen | 73/421.5 R |
| 3,757,583 | 9/1973 | Ludewig, Jr. | 73/421.5 R |

Primary Examiner—S. Clement Swisher
Attorney, Agent, or Firm—John O. Tresansky; Robert D. Marchant; John R. Manning

[57] ABSTRACT

A fluid sampling device for selectively sampling multiple fluids including a support frame. A plurality of fluid inlet devices extend through the support frame and each of the fluid inlet devices include a longitudinal aperture extending therethrough. An opening device that is responsive to a control signal selectively opens the aperture for passing the fluid therethrough. A closing device that is responsive to another control signal selectively closes the aperture for terminating further fluid flow therethrough.

21 Claims, 6 Drawing Figures

FLUID SAMPLING DEVICE

ORIGIN OF THE INVENTION

The invention described herein was made by an employee of the United States Government and may be manufactured and used by or for the Government for governmental purposes without the payment of any royalties thereon or therefore.

BACKGROUND OF THE INVENTION

1. Field of the Invention

This invention relates generally to inlet leaks for sampling gases and more particularly to a fluid sampling device for selectively sampling multiple fluids.

2. Description of the Prior Art

Inlet leaks are highly useful and extensively used for introducing a fluid such as, for example, a gas into a mass spectrometer or other devices for analyzing a gas in a particular environment.

Present day devices utilize a single inlet leak tube constructed of glass having a capillary opening extending through the glass tube. The inlet leak is inserted into a mass spectrometer or other gas analyzers. The apparatus is placed within the gas to be analyzed and the gas is allowed to flow through the inlet leak into the gas analyzer where the characteristics of the gas can be broken down and studied. This device works exceptionally well where a single particular gas is to be analyzed.

In certain environmental situations the above device has many disadvantages because a single inlet tube can only be used once since it is contaminated by the gas that has been sampled. A use where such prior art devices is unsuitable involve sampling of multiple gases at different locations. If the above prior art devices are used, the sample taken at the first location can be analyzed correctly, however, subsequent samples taken at different locations will be contaminated by the residue gas from the first location. This will prevent a true analysis of the gases at the subsequent locations. Thus, the inlet leak tube can only be used once or only be used to analyze the same gas again and once the inlet leak tube is opened gases will continue to flow into the analyzer.

To take multiple samples of gases without contamination by the previously sampled gas it is necessary to replace the used inlet leak tube with an unused inlet leak tube and the analyzer must be pumped out to remove the residual gases or a plurality of gas analyzers may be used having a single uncontaminated inlet leak tube. In many situations the above multiple sampling technique cannot be used or are impractical and expensive. An exemplary situations is where the gas samples in a planets atmosphere must be taken at different heights above the planets surface. Since planet probes are unmanned, it would be difficult to provide for the replacement of the inlet leak tube after each gas sample is taken, and because of size and weight limitations on a spacecraft multiple gas analyzers having a single one-shot inlet leak tube cannot be used.

Another situation where the above prior art devices are unfeasible is in analyzing the different gases emitted by a volcano at various heights and at different times within the volcano. Time is of the essence when working around an active volcano and it is therefore desirable to obtain and analyze the gas samples as quickly as possible. The above prior art devices do not lend themselves to such rapid sampling.

OBJECTS OF THE INVENTION

Accordingly, one object of this invention is to provide a novel apparatus for sampling a fluid.

Another object of the present invention is to provide a novel fluid sampling device capable of sampling multiple fluids.

Still another object of this invention is to provide a novel fluid sampling device capable of sampling multiple fluids without becoming contaminated.

A further object of the instant invention is to provide a new and improved fluid sampling device for selectively sampling different fluids without removing used inlet leak tubes.

A still further object of this invention is to provide a new and improved fluid sampling device that selectively and accurately samples multiple fluids with a single gas analyzer.

Another still further object of this invention is to provide a new and improved relatively inexpensive and compact fluid sampling device for selectively sampling multiple fluids.

SUMMARY OF THE INVENTION

Briefly, in accordance with one embodiment of this invention, these and other objects are attained by providing a fluid sampling device that selectively samples multiple fluids. The fluid sampling device generally includes a support frame which is attached to a single fluid analyzer such as a mass spectrometer. A plurality of fluid inlet devices extend through the support frame. Each fluid inlet device has a longitudinal aperture extending therethrough into the fluid analyzer. An opening device is responsive to a control signal for selectively opening the aperture for passing the fluid therethrough. A closing device is responsive to another control signal for selectively closing the aperture for terminating further fluid flow therethrough.

The above and further objects of the invention will appear more fully from the following detailed description when the same is red in conjunction with the accompanying drawings. It is to be understood, however, that the drawings are not intended as a definition of the invention but are for the purpose of illustration only.

BRIEF DESCRIPTION OF THE DRAWINGS

In the drawings where like parts are designated by like references.

DESCRIPTION OF THE PREFERRED EMBODIMENT

Figure 1:
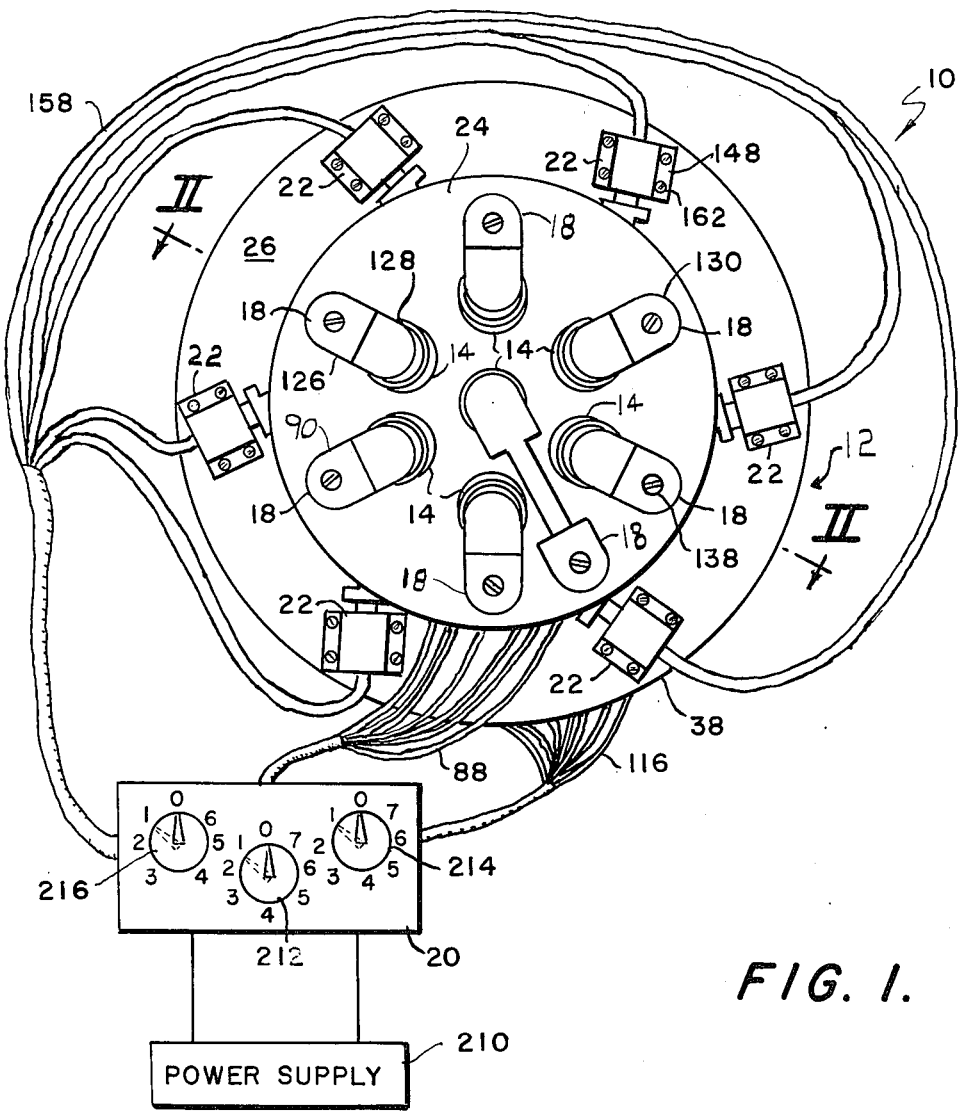
FIG. 1 is a top view of the fluid sampling device of the present invention showing the plurality of fluid inlet devices, opening devices, closing devices, control panel, and signal generating device.

Referring to FIG. 1, the invention generally includes a fluid sampling device, denoted generally by numeral 10, for selectively sampling multiple fluids. Fluid sampling device 10 includes a support frame, denoted generally by numeral 12, with a plurality of fluid inlet devices 14 extending through the support frame 12. Each fluid inlet device 14 has a longitudial aperture 16 (FIG. 3) extending longitudinally therethrough. An opening device 18 is responsive to a control signal supplied by control panel 20 for selectively opening aperture 16 for passing the fluid therethrough. A closing device 22 is responsive to another control signal supplied by control panel 20 for selective closing aperture 16 for terminating further fluid flow therethrough.

Figure 2:
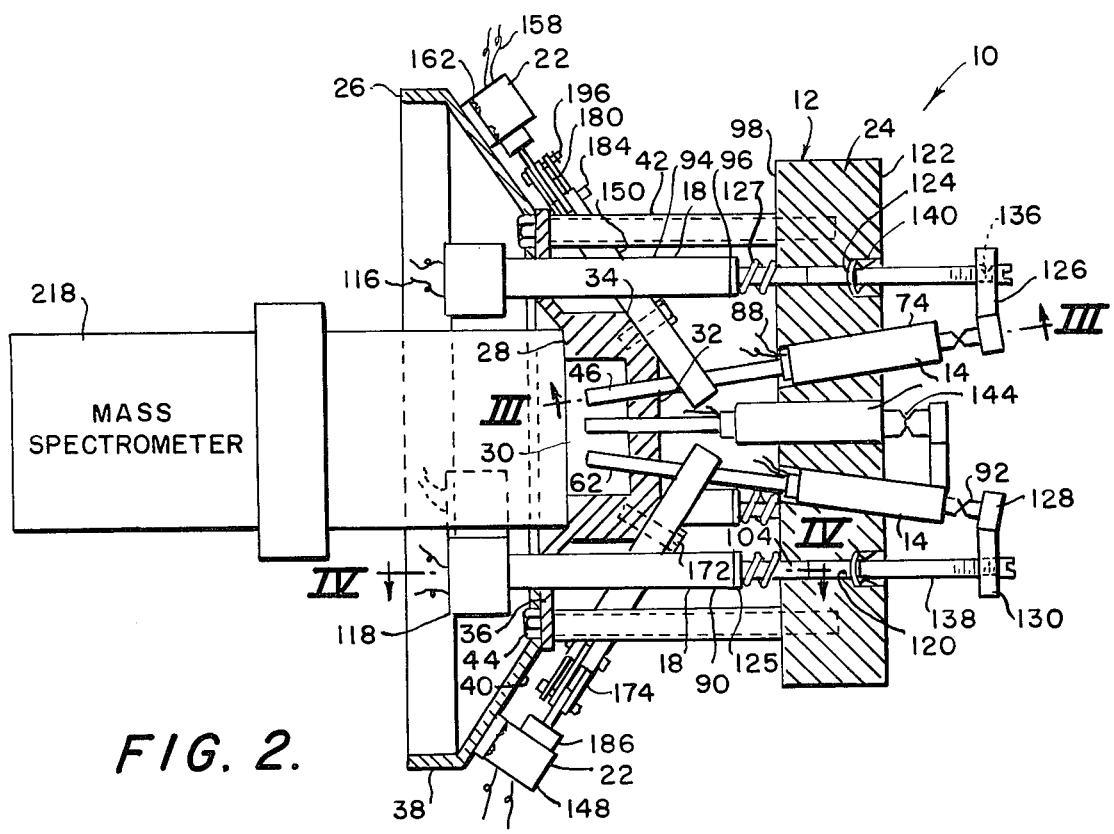
FIG. 2 is a side view, in cross section, of the fluid sampling device taken along the lines II — II of FIG. 1 showing the interconnections between the fluid inlet devices, opening devices and closing devices.

Referring now to FIGS. 1 and 2, support frame 12 of fluid sampling device 10 includes a first flange 24 and a second flange 26 spaced from and connected to flange 24 so that the flanges are axially aligned. Flange 24 is preferably, circular, however, any shape may be used depending on the specific design criteria. Flange 26 is formed of a central circular support 28 having an outer diameter substantially smaller than the outer diameter of flange 24 and having an inner cavity 30. An outer surface 32 of support 28 includes a beveled surface 34 of the outer periphery. Flange 26 further includes an outwardly extending flange 36 having an outer diameter less than the diameter of flange 24. Flange 26 additionally includes a support disc 38 having an outer diameter substantially greater than the diameter of flange 24 and a central opening having a diameter substantially greater than circular support 28 and less than the diameter of outwardly extending flange 36. Support disc 38 is connected to flange 36, in a conventional manner such as by bolting or welding (not shown) so that surface 40 forms an acute angle to outwardly extending flange 36. Although support disc 38 is preferably a separate part from outwardly extending flange 36 it should be understood, that it may be formed integrally with flange 36, if desired.

Second flange 26 is spatially secured to first flange 24 by spacer sleeves 42 and bolts 44 which extend between flange 36 and flange 24. Bolts 44 extend through outwardly extending flange 36, sleeves 42 and screw into flange 24. Sleeves 42 separate flanges 24 and 26 while bolts 44 hold them rigidly together.

The plurality of fluid inlet devices 14 are shown as extending through flange 24 and circular support 28 of flange 26. As shown in FIG. 1 six fluid inlet devices 14 are spaced in a circular configuration around flange 24 and a seventh is centered in flange 24. It should be understood, that the number and configuration of fluid inlet devices 14 shown is for illustrative purposes only. It is preferred that the six fluid inlet devices 14 be inclined at an angle so that the lower portion 46 of each fluid inlet device 14 extends through circular support 28 and into inner cavity 30.

Figure 3:
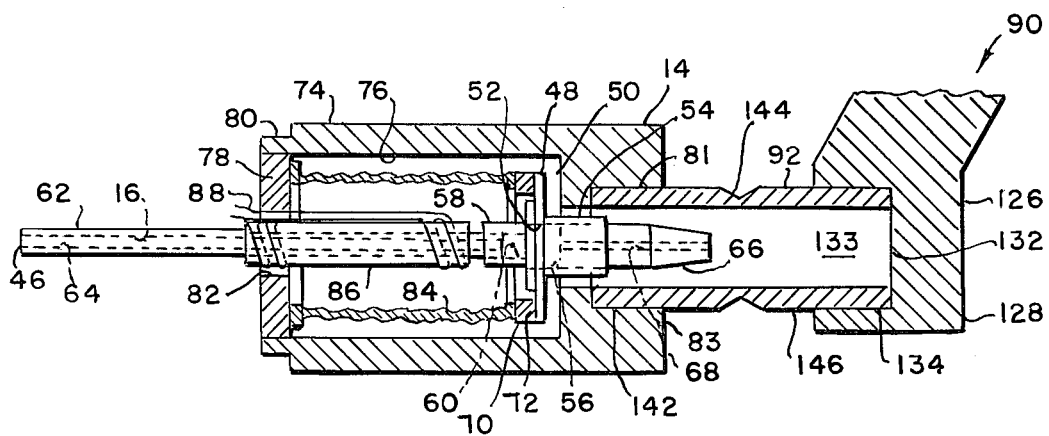
FIG. 3 is a side view, in cross section, of the fluid inlet devices taken along the lines III — III of FIG. 2 showing the internal components of the fluid inlet devices and shearing device of the opening device.

As more clearly shown in FIG. 3 each fluid inlet device 14 includes a circular holder 48 having a circular disc 50 with an opening 52 extending therethrough. A first cylindrical shoulder portion 54 is secured to disc 50, such a by welding, so that an opening 56 is in axial alignment with opening 52 in disc 50. A second cylindrical shoulder portion 58 is secured to the opposite side of disc 50, such as by welding, to position an opening 60 in axial alignment with opening 52 in disc 50 and opening 56 in shoulder portion 54. A deformable tube 62 is inserted within opening 60 of shoulder portion 58 and secured therein, such as by welding. Deformable tube 62 includes an opening 64 extending therethrough and in axial alignment with opening 60 of shoulder portion 58. End 46 of tube 62 extends through support 28 of flange 26 and into inner cavity 30 and is secured to support 28, such as by welding. A fluid receiving insert 66 having a capillary opening 68 extending therethrough is inserted within opening 56 of shoulder portion 54 and secured thereto in any well known and conventional manner.

It is important when bonding metal to glass, especially in inlet leaks, that a proper seal between the glass and metal be made and that the integrity of the seal be maintained over a wide temperature range and under other hazardous environmental conditions. It is therefore necessary that a metal and glass be used that have substantially the same coefficient of expansion characteristics. KOVAR metal and certain glass compositions have been found to posses substantially the same coefficient of expansion and not to degrade under harsh environmental conditions. It is preferable that circular holder 48 be made from the metal KOVAR being composed of substantially 54% Fe, 29% Ni, and 17% Co and that fluid receiving insert 66 be composed of glass having a composition range of 65 – 70% Si $O_2$, 3 – 7% $Al_2 O_3$, 17 – 18% $B_2 O_3$, 1% $Li_2 O$, 1% – 2% $Na_2 O$, and 2 – 8% $K_2 O$. Although a glass insert made in the composition range above is acceptable the preferred composition of the glass insert is 70% $SiO_2$, 3% $Al_2 O_3$, 17% $B_2 O_3$, 1% $Li_2 O$, 1% $Na_2 O$ and 8% $K_2 O$. Further, it is preferred that deformable tube 62 be made from conventional stainless steel since it may be subjected to harsh environmental conditions. Although the above compositions are preferred it should be understood, that other materials may be used as long as the integrity of the seal is maintained over a wide temperature range and the material does not degrade under harsh environmental conditions.

Fluid inlet devices 14 further include a metal flange or ring 70 having an outer diameter substantially the same as the outer diameter of circular disc 50 and secured to surface 72 of disc 50, such as by welding. A sleeve 74 surrounds glass insert 66, holder 48, and a portion of tube 62, and has an inner diameter substantially greater than the outer diameter of disc 50 thereby forming an annular space 76. Sleeve 74 is affixed to first flange 24 of support frame 12, such as by welding, and includes an inwardly extending flange 78 secured to end 80 such as by welding. Flange 78 includes an inner diameter substantially greater than the outer diameter of tube 62 forming a space 82 therebetween. Although flange 78 is shown as a separate ring, it may also be formed integrally with sleeve 74. Sleeve 74 further includes a recessed opening 81 in end 83. A metal cylinderical bellows 84 surrounds tube 62 within space 76 and extends between flange 78 and ring 70. Bellows 84 is secured to flange 78 and ring 70 as by welding and provides a rigid base for supporting tube 62, holder 48, and glass insert 66 within sleeve 74.

Fluid inlet devices 14 further includes an insulating coating 86 surrounding the portion of tube 62 which is surrounded by sleeve 74. If desired, insulating coating 86 may extend beyond flange 78, as shown in FIG. 3. Insulating coating 86 may be a conventional type having electrical insulating properties and may be applied in any conventional manner. It is preferred, however, that insulating coating 86 be formed of ceramic and plasma sprayed on tube 62. The thickness of insulating coating 86 should be sufficient for space 82 to remain between insuating coating 86 and flange 78. An electrical heating wire 88 is wound on insulating coating 86 and the ends thereof extend through space 82 for connection to control panel 20. If desired, additional ceramic insulating coating may be applied on top of heating wire 88 to provide for additional electrical insulation. Any type of electrically conducting wire may be used as a heating element, however, it is preferred that heating wire 88 be made of tungsten. When activated by control panel 20 heating wire 88 heats tube 62 to a temperature above the evaporation point of the fluid to be sampled to thereby drive off any fluid clinging to tube 62 prior to the fluid flowing through aperture 16. In addition to supporting tube 62, holder 48, and glass insert 66, bellows 84 provides thermal isolation for fluid inlet devices 14 to reduce the rate of heat loss from heating wire 88. More specifically, bellows 84 provides a high resistance thermal path through tube 62 which reduces the heat loss from heater wire 88.

The opening device 18 associated with each fluid inlet device 14 is selectively activated by a control signal from control panel 20 so that each opening device 18 exposes aperture 16 of each fluid inlet tube 14 only when a specific fluid sample is to be taken.

Opening device 18 includes an actuator device, generally indicated by numeral 90, which is connected to and extends through first and second flanges 24 and 26 and is connected to control panel 20 and a shearing device 92 which severably interconnects and is insealing engagment with actuator device 90 and fluid inlet device 14.

Actuator device 90 includes a cylinder 94 which extends through outwardly extending flange 36 of flange 26 adjacent to each fluid inlet device 14. Cylinder 94 is secured to flange 36, as by welding, so that end 96 thereof is spaced below surface 98 of flange 24. As more clearly shown in FIG. 4 a first piston 97 is in sliding engagement with inner surface 102 of cylinder 94. A first rod 99 is secured to piston 97 such as by welding. A support rod 108 secured to surface 102, as by welding, surrounds rod 99 and is in sliding engagement therewith. A second piston 100 is spaced from rod 99 and support ring 108 and is in sliding engagement with surface 102. A second rod 104 is secured to piston 100, as by welding, and extends above end 96. A seal ring 106 is secured to surface 102 at end 96, as by welding, so that rod 104 is in sliding engagement therewith. An expander 112 is contained within cylinder 94 below piston 97. Preferably expander 112 is formed of a pyrotechnic material which when heated burns to cause a gas to be formed which expands and pushes piston 97 until it contracts support ring 108. As piston 97 moves, rod 99 contracts piston 100 causing piston 100 to move toward end 96 of cylinder 94. Although the preferred actuator device 90 includes a dual piston and rod arrangement as shown, it should be understood, however, that other arrangements can also be used. For example, actuator device 90 can have a single piston and rod in which case support ring 108 is replaced with an orifice ring and expander material 112 occupies the space below the orifice ring.

Expander 112 is electrically connected by an igniter wire 116 extending through end 114 to control panel 20 so that actuator device 90 may be selectively activted by a control signal from control panel 20. Although expander 112 is preferably a pyrotechnic material it should be understood that any type of device may be used such as, for example, a compressed spring wherein upon activation by control panel 20 a release mechanism releases the compressed spring to expand in contact with piston 97 causing rod 99 to contact piston 100 and slide piston 100 toward end 96. In the preferred device, a restrainer block 118 is screwed onto end 114 of cylinder 94 to prevent cylinder 94 from bursting upon ignition of expander 112.

Flange 24 contains a plurality of openings 120 extending therethrough and in axial alignment with each rod 104. In the relaxed position, that is, before activtion of expander 112, rod 104 extends into opening 120 and is in sliding engagement with flange 24. As opening 120 approaches surface 122 of flange 24 the diameter thereof is substantially increased to enable a flexible diaphragm 124 to be seated therein thereby sealing opening 120 between surfaces 98 and 122. To prevent rod 104 from puncturing diaphragm 124 when actuator device 90 is activated a collar 125 is secured to rod 104, as by welding, between end 96 of cylinder 94 and surface 98 of flange 24. Colar 125 is positioned so that when actuator device 90 is activated rod 104 will slide within opening 120 and flex diaphragm 124 but collar 125 will contact surface 98 and stop further movement of rod 104 before rod 104 punctures diaphragm 124. Further, a flexible spring 127 surrounds rod 104 between surface 98 and collar 125 to maintain tension on collar 125 to keep it in contact with end 96 prior to activation of actuator device 90. Thus, rod 104 will not slide in and out of cylinder 94 prior to activation of actuator device 90.

Actuator device 90 further includes a contact plate 126 having a first end 128 connected to shearing device 92 and a second end 130 spaced from and in alignment with opening 120. End 128 includes a recess 132 wherein one end 134 of shearing device 92 is seated. End 130 has a threaded opening 136 extending therethrough and in axial alignment with opening 120 in flange 24. For fluid inlet device 14 which are placed in a circle around surface 122 of flange 24, end 128 is formed at an angle to end 130 to be in alignment with shearing device 92 and opening 120, respectively, since these fluid inlet tubes 14 are formed at an angle to cylinder 94. The center fluid inlet device 14 is not formed at an angle to cylinder 94 and thus end 128 is not formed at an angle to end 130. Contact plate 126 further includes an adjusting screw 138 threated into opening 136 and extends into opening 120 in flange 24 and is adjusted until it touches diaphragm 124. A guide ring 140 is secured such as by a press fit, within opening 120 above diaphragm 124 and is in sliding contact with adjusting screw 138. Guide ring 140 guides adjusting screw 138 within the enlarged portion of opening 120.

Shearing device 92 is preferable tubular having a central opening 133 extending therethrough and is connected between contact plate 126 of actutor device 90 and sleeve 74 of fluid inlet device 14. One end 134 of shearing device 92 fits within recess 132 of end 128 on contact plate 126 and is secured and sealed therein as by brazing. The other end 142 of shearing device 92 fits within recessed opening 81 of end 83 on sleeve 74 so that glass insert 66 extends within opening 133 and is secured and sealed therein as by brazing. Shearing device 92, preferable includes a V-shaped notch 144 substantially midway between ends 134 and 142 and circumferentially extending around the outer periphery 146 thereof so that upon activation of actuator device 90, shearing device 92 will shear at the V notch. Shearing device 92 is preferably made from a hard and brittle material such as ceramic so that it is easily snapped at V notch 144 when a shearing force is applied thereto. Other hard and brittle materials may also be used such as, for example, glass, brick, and porcelain.

Figure 5:
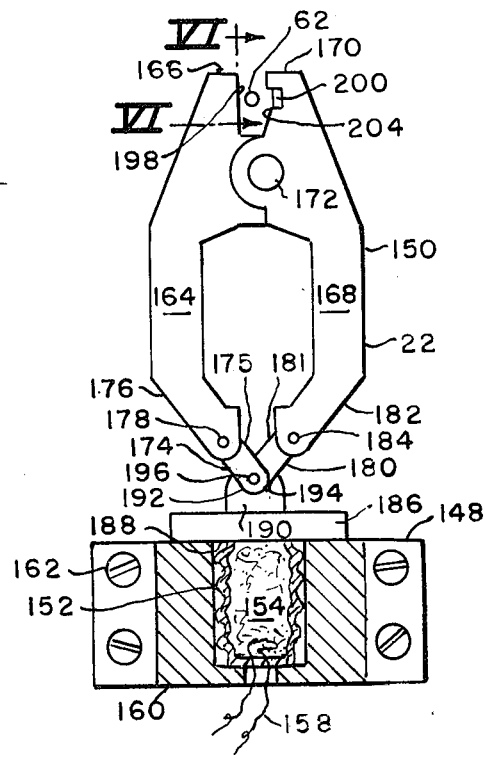
FIG. 5 is a side view of the closing device of FIG. 2 showing the moveable clamping mechanism and the actuator device, in cross section.

Closing device 22 is associated with each fluid inlet device 14 that is circularly spaced and inclined to surface 122 of flange 24. Preferably, the central fluid inlet device 14 does not have an associated closing device 22 as will be explained hereinafter. As clearly shown in FIG. 5 closing device 22 includes an actuator 148 and a movable clamp 150. Actuator 148 includes an expandable bellows 152 wherein an expander 154 is contained. Expander 154 is preferably made of a material such that when ignited a gas is formed to expand bellows 152. An igniter wire 158 extends from expander 154 to control panel 20 so that upon command a control signal from control panel 20 passes through igniter wire 158 and ignites expander 154 which expands bellows 152. A housing 160 surrounds bellows 152 in a manner whereby the sides of bellows 152 are in contact with the sides of housing 160. This causes bellows 152 to expand along its longitudinal axis rather than expanding laterally. Housing 160 is secured to surface 40 of support disk 38, such as by screws 162, so that the longitudinal axis of bellows 152 substantially intersects deformable tube 62 between circular support 28 and flange 24.

Movable clamp 150 includes a first arm 164 having a first end 166 adjacent to and overlapping tube 62. A second arm 168 has a first end 170 adjacent to and overlapping tube 62 oppositely positioned from end 166 of arm 164. First and second arms 164 and 168 are pivotably connected together below ends 166 and 170, respectively, by bolt 172. A first linking bar 174 is pivotably connected at one end 175 to a second end 176 of arm 164 by a pivot pin 178. A second linking bar 180 is pivotably connected at one end 181 to a second end 182 of arm 168 by a pivot pin 184. A support platform 186 abuts actuator 148 so that surface 188 is in contact with bellows 152. Support platform 186 includes a flange 190 extending therefrom. Flange 190 and the other ends 192 and 194 of linking bars 174 and 180, respectively, are pivotably connected together by a pivot pin 196. Arms 164 and 168 abut beveled surface 34 of circular support 28 and are secured thereto by pivot bolt 172.

Figures 4, 6:
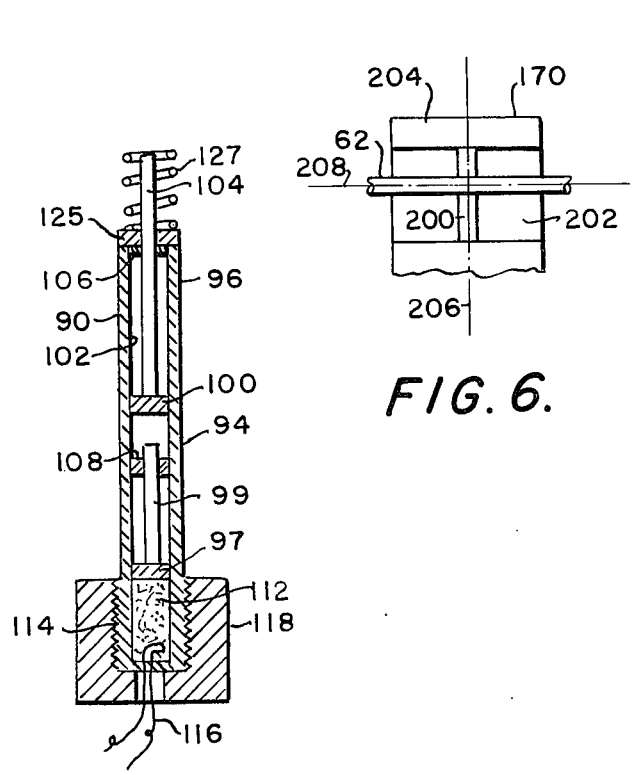
FIG. 4 is a side view, in cross section, of the actuator device taken along the lines IV — IV of FIG. 2 showing the cylinder, piston, rod, and expander.
FIG. 6 is a top view of one arm of the moveable clamping mechanism taken along the lines VI—VI of FIG. 5 showing the land extending transverse to the deformable tube.

End 166 of arm 164 includes a substantially flat surface 198 adjacent to tube 62. As shown in FIG. 6 end 170 of arm 168 includes a land 200 and a pair of grooves 202 on each side of land 200. Land 200 is formed on surface 204 of end 166 which is adjacent to tube 62 and formed such that the longitudinal axis 206 thereof is transverse to the longitudinal axis 208 of tube 62. When bellows 152 expands it causes support plate 186 to move which causes linking bars 174 and 180 to expand outwardly thereby causing arms 164 and 168 to pivot about bolt 172 closing ends 166 and 170 against tube 62. Land 200 deforms and pinches tube 62 against surface 198 closing opening 64 in tube 62.

Referring to FIG. 1, control panel 20 is any well known and conventional electronic control and power supply system 210 such as, for example, a D.C. power supply. Control panel 20 includes three selector switches 212, 214, and 216. When selector switch 212 is switched to position 1, it completes an electrical circuit between power supply 210 and one heater 88 associated with the first fluid inlet device 14 to be activated for use. When selector switch 214 is switched to position 1, it completes an electrical circuit between power supply 210 and one actuator device 90 of the opening device 18 associated with the first fluid inlet device 14 to be opened to the fluid to be sampled. When selector switch 216 is switched to position 1, it completes an electrical circuit between power supply 210 and one actuator device 148 of the one closing device 22 associated with the first fluid inlet device 14 to be closed upon completion of the fluid sample taking. Selector switches 212 and 214 are switched sequentially from position 1 to 7 which selectively activates in sequence heaters 88 and actuator devices 90 for selectively opening at different times each of the seven fluid inlet devices 14. Selector switch 216 is switched sequentially from positions 1 to 6 which selectively activates in sequence the first six actuator devices 148 for selectively closing each of the first six fluid inlet devices 14 before the next fluid inlet device 14 is opened. The last fluid inlet device 14 need not be closed since no further samples can be taken by fluid sampling device 10. Selector switches 212, 214, and 216 may be switched by conventional dial switches as shown in FIG. 1 or may be activated remotely by electromagnet signals such as radio waves or by light signals such as emitted by LASERS. The only requirement being that it having switching capabilities so that each fluid inlet device 14, opening device 18, and closing device 22 can be individually and selectively activated.

In operation, fluid sampling device 10 is connected in a conventional manner to a fluid analyzer such as, for example, a gas mass spectrometer 218 so that inner cavity 30 of flange 26 is opened to gas analyzing components of the mass spectrometer. It is preferred that a conventional gas cleaning device (not shown) be incorporated with mass spectrometer 218 to purge and remove the excess sampled gas therefrom prior to introducing a new gas sample. It is also preferred that fluid sampling device 10 and mass spectrometer 218 be enclosed within a gas tight structure (not shown) whereby only surface 122 of flange 24 will be exposed to the various gases to be sampled. This will protect the various components of fluid sampling device 10 from attack by harmful environmental conditions.

When a first sample is to be taken, switch 212 on control panel 20 is turned to position 1 which causes an electrical current to flow from power supply 210 only through the electrical heating wire 88 in the first fluid inlet device 14 to be used to take a gas sample. The electrical current heats heating wire 88 which, in turn, heats insulating coating 86 and metal tube 62. The heat drives off any contaminated gases that may have adhered to opening 64 in metal tube 62. The driven off gases are absorbed by the gas cleaning device in the conventional manner.

After metal tube 62 has been purged, switch 214 on control panel 20 is turned to position 1 which sends an electrical current from power supply 210 only through wire 116 associated with actuator 90 of the first fluid inlet device 14 to cause wire 116 to ignite expander material 112 causing it to release a gas. As the gas expands it pushes on piston 97 causing it and rod 99 to slide upward in cylinder 94 until piston 97 contacts support ring 108. As rod 99 slides upward it contacts piston 100 causing it and rod 104 to slide upward in cylinder 94. Rod 104 slides upward in opening 120 compressing spring 127 between collar 125 and surface 98 until rod 104 contacts diaphragm 124. Diaphragm 124 provides a seal within opening 120 to prevent the outside gases from flowing through opening 120 and into the interior of fluid sampling device 10 while at the same time providing the flexibility to allow movement of adjusting screw 138 by rod 104. Diaphragm 124 flexes under pressure by rod 104 and pushes against adjusting screw 138 causing adjusting screw 138 to slide upward against guide ring 140. Rod 104 is prevented from rupturing diagragm 124 by collar 125 and spring 127 coming in contact with surface 98. This upward movement of adjusting screw 138 imparts a rotational moment to contact plate 126. This bending moment of contact plate 126 imparts a shearing force to tubular shearing device 92 causing it to shear or break at V notch 144 thereby exposing glass insert 66 and central opening 16 to the gas to be sampled. The gas to be sampled flows through central opening 16 in fluid inlet device 14 and into inner cavity 30 in flange 26. The gas thereupon flows into mass spectrometer 218. The gas is prevented from flowing into the interior of fluid sampling device 10 by bellows 84 since the gas can only flow between bellows 84 and sleeve 74.

Upon completion of the gas analysis by mass spectrometer 218, switch 216 is turned to position 1 which sends an electrical impulse from power supply 210 through wire 158 associated with actuator device 148 of the closing device 22 which is adjacent to the first fluid inlet device 14 to ignite expander 154. As expander 154 burns the gases developed expands bellows 152. Bellows 152 presses against support plateform 186 moving support plateform 186. The movement of of support platform 186 causes linking bars 174 and 180 to pivot about pivot pin 196 and about pivot pins 118 and 184, respectively. This pivoting action causes ends 176 and 182 of arms 164 and 168 respectively, to separate due to the arms pivoting about one another at pivot bolt 172. As ends 176 and 182 separate, ends 166 and 170 of arms 164 and 168, respectively, close causing flat surface 198 and land 200 to contact metal tube 62. Ends 166 and 170 continue to close until land 200 deforms metal tube 62 and pinches opening 64 shut to close central opening 16 and preventing any gas from flowing through central opening 16 into mass spectrometer 218. Preferably, linking bars 174 and 180 pivot to slightly over center to lock ends 166 and 170 in the closed position to ensure no leakage of gas through central opening 16. After central opening 16 is closed the conventional gas cleaning device (not shown) purges mass spectrometer 218.

When a second gas sample is to be taken, selector switch 212 of control panel 20 is turned to position 2 which heats a second heater wire 88 around a new fluid inlet device 14. The sequence of events for opening and closing the second fluid inlet device 14 is identical to that hereinbefore described for the first fluid inlet device 14. This cycle continues until all fluid inlet devices 14 have been used. When the seventh and last fluid inlet device 14 has been opened such as, for example, the central fluid inlet device 14 as shown in FIGS. 1 and 2, there is no need to close central opening 16 following the gas analysis since no further gas samples can be taken. Thus, closing device 22 can be eliminated for the last fluid inlet device 14.

There has been disclosed a fluid sampling device for selectively sampling multiple fluids. The problems associated with taking and analyzing different fluids or fluids at different locations have been eliminated by providing a device with a plurality of fluid sampling inlet devices that are selectively opened and closed to surrounding fluids thereby permitting sampling of numerous fluids by a single fluid analyzer.

Accordingly, the invention having been described in its best embodiment and mode of operation, that which is desired to be claimed by Letters Patent is:

1. A fluid sampling device for selectively sampling multiple fluids comprising:
   a support frame;
   a plurality of fluid inlet means extending through said support frame, each of said inlet means having an aperture extending therethrough;
   means responsive to a control signal for selectively opening said aperture for passing said fluid therethrough; and
   means responsive to another control signal for selectively closing said aperture for terminating further fluid flow therethrough.

2. The fluid sampling device of claim 1 wherein said support frame includes:
   a first flange having a plurality of openings extending thererthrough for receiving a portion of each of said fluid inlet means; and
   a second flange spaced from and axially aligned with said first flange and having a plurality of openings extending therethrough for receiving another portion of each of said fluid inlet means.

3. The fluid sampling device of claim 1 wherein each of said fluid inlet means includes:
   tube means having a portion of said aperture longitudinally extending therethrough;
   fluid receiving means having another portion of said aperture longitudinally extending therethrough;
   means for holding said tube means and said fluid receiving means for maintaining a substantially axial alignment of another portion of said aperture in said fluid receiving means; and
   sleeve means surrounding said fluid receiving means, holding means and a portion of said tube means and forming an annular space therebetween.

4. The fluid sampling device of claim 3 wherein each of said fluid inlet means further includes:
   an insulating coating surrounding said portion of said tube means within said sleeve means; and
   an electrical heater surrounding a portion of said insultor coating and responsive to an additional control signal for removing contaminated fluids from said tube means.

5. The fluid sampling device of claim 4 wherein:
   said holder means includes an outwardly and circumferentially extending flange within said annular space; and
   said sleeve means includes an inwardly and circumferentially extending flange axially spaced from said flange on said holder means.

6. The fluid sampling device of claim 5 wherein each of said inlet means further includes a bellows within said annular space and surrounding said tube means, said bellows being connected between said outwardly extending flange and said inwardly extending flange for providing thermo isolation of said tube means to reduce heat loss from said electrical heater.

7. The fluid sampling device of claim 3 wherein said fluid receiving means and said holder means have substantially the same coefficient of expansion.

8. The fluid sampling device of claim 7 wherein said fluid receiving means is formed from a material having a composition in the range of 65-70% SiO$_2$, 3-18% B$_2$O$_3$, 1% Li$_2$O, 1-2% Na$_2$O$_1$ and 2-8% K$_2$O.

9. The fluid sampling device of claim 7 wherein said fluid receiving means is formed from a material having a composition substantially of 70% S$_i$O$_2$, 3% Al$_2$O$_3$, 17% B$_2$O$_3$, 1% Li$_2$O, 1% Na$_2$O and 8% K$_2$O.

10. The fluid sampling device of claim 7 wherein said holder mans is formed from a material having a composition substantially of 54% Fe, 29% Ni, and 17% Co.

11. The fluid sampling device of claim 1 wherein each of said opening means includes:
actuator means adjacent to each of said fluid inlet means and responsive to said control signal; and
shearing means in sealing engagement between said actuator means and said fluid inlet means, said shearing means being separated upon activation of said actuator means by said control signal for exposing said aperture to said fluid.

12. The fluid sampling device of claim 11 wherein said actuator means includes:
a cylinder;
a first movable piston within said cylinder;
a first rod connected to said piston;
a second movable piston within said cylinder axially aligned with and spaced from said first rod;
a second rod connected to said second piston and having a portion thereof within said cylinder and another portion thereof extending from a first end of said cylinder;
an expander within said cylinder between said first piston and a second end of said cylinder and being responsive to said control signal; and
a contact plate having one end in sealing engagement with said shearing means and another end spaced from and in alignment with said second rod.

13. The fluid sampling device of claim 12 wherein said fluid inlet means and said shearing means are formed at an angle to each of said actuator means.

14. The fluid sampling device of claim 11 wherein said shearing means is tubular.

15. The fluid sampling device of claim 14 wherein said shearing means includes an intermediately located weakened portion.

16. The fluid sampling device of claim 15 wherein said shearing means is formed of ceramic.

17. The fluid sampling device of claim 1 wherein each of said closing means includes;
actuator means adjacent to each of said fluid inlet means and responsive to said another control signal; and
movable clamping means responsive to said actuator means and having a portion thereof overlapping a portion of said fluid inlet means for deforming said portion of said fluid inlet means and closing said aperture upon activation by said actuator means.

18. The fluid sampling device of claim 18 wherein said actuator means includes;
a bellows; and
an expander within said bellows which is responsive to said another control signal for expanding said bellows upon activation by said another control signal.

19. The fluid sampling device of claim 17 wherein said portion of said fluid inlet means is a deformable tube.

20. The fluid sampling device of claim 19 wherein said movable clamping means includes:
a first arm having a first end overlapping said deformable tube;
a second arm pivotably connected to said first arm and having a first end overlapping said deformable tube oppositely positioned from said first end of said first arm;
a first linking bar pivotably connected at one end to a second end of said first arm;
a second linking bar pivotably connected at one end to a second end of said second arm; and
a support platform abutting said actuator means and pivotably connected to the other ends of said first and second linking bars.

21. The fluid sampling device of claim 20 wherein said first end of said first arm includes a substantially flat surface adjacent to said deformable tube and said first end of said second arm includes a land adjacent to said deformable tube and having the longitudinal axis of said land transverse to the longitudinal axis of said deformable tube.

* * * * *